(12) United States Patent
Greenhut et al.

(10) Patent No.: US 9,789,317 B2
(45) Date of Patent: Oct. 17, 2017

(54) PACING CROSSTALK DETECTION

(71) Applicant: Medtronic, Inc., Minneapolis, MN (US)

(72) Inventors: Saul E Greenhut, Aurora, CO (US); Wade M Demmer, Coon Rapids, MN (US); Todd J Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/632,317

(22) Filed: Feb. 26, 2015

(65) Prior Publication Data

US 2016/0250478 A1    Sep. 1, 2016

(51) Int. Cl.
*A61N 1/36* (2006.01)
*A61N 1/365* (2006.01)
*A61N 1/37* (2006.01)

(52) U.S. Cl.
CPC ........... *A61N 1/36514* (2013.01); *A61N 1/37* (2013.01)

(58) Field of Classification Search
None
See application file for complete search history.

(56) References Cited

U.S. PATENT DOCUMENTS

| 4,825,870 | A | 5/1989 | Mann et al. |
| 4,974,589 | A | 12/1990 | Sholder |
| 5,366,488 | A | 11/1994 | Franberg et al. |
| 5,507,782 | A | 4/1996 | Kieval et al. |
| 5,683,432 | A | 11/1997 | Goedeke et al. |
| 5,776,167 | A | 7/1998 | Levine et al. |
| 5,782,881 | A | 7/1998 | Lu et al. |
| 6,128,532 | A | 10/2000 | Stoop et al. |
| 6,167,307 | A * | 12/2000 | Hess ................... A61N 1/3627 607/9 |
| 6,442,433 | B1 | 8/2002 | Linberg |
| 6,754,592 | B2 | 6/2004 | Morrow et al. |
| 6,871,095 | B2 | 3/2005 | Stahmann et al. |
| 7,120,494 | B2 | 10/2006 | Stahmann et al. |
| 8,005,539 | B2 | 8/2011 | Burnes et al. |
| 8,433,409 | B2 | 4/2013 | Johnson et al. |

(Continued)

FOREIGN PATENT DOCUMENTS

| EP | 1 302 215 A2 | 4/2003 |
| WO | 2010/051424 A1 | 5/2010 |

OTHER PUBLICATIONS (PCT/US2016/019872) PCT Notification of Transmittal of the International Search Report and the Written Opinion of the International Searching Authority.

(Continued)

*Primary Examiner* — Ankit D Tejani

(57) ABSTRACT

An implantable pacemaker is configured to sense a cardiac electrical signal received by a pair of electrodes coupled to the pacemaker, start a pacing escape interval to control a time that a pacing pulse is delivered in a heart chamber, and detecting if the sensed cardiac electrical signal is a crosstalk event that is an electrical pulse delivered to the patient by a different device than the implantable pacemaker. The implantable pacemaker withholds restarting the pacing escape interval in response to sensing the cardiac electrical signal based on detecting the sensed cardiac electrical signal as the crosstalk event.

18 Claims, 6 Drawing Sheets

(56) References Cited

U.S. PATENT DOCUMENTS

| | | |
|---|---|---|
| 8,532,785 B1 | 9/2013 | Crutchfield et al. |
| 8,541,131 B2 | 9/2013 | Lund et al. |
| 2008/0027491 A1 | 1/2008 | Sheldon et al. |
| 2010/0114224 A1* | 5/2010 | Krause ............... A61N 1/36521 607/8 |
| 2010/0324622 A1* | 12/2010 | Gilkerson ............ A61N 1/3706 607/17 |
| 2011/0257699 A1* | 10/2011 | Gilkerson ............ A61N 1/3702 607/27 |
| 2011/0301656 A1* | 12/2011 | Casavant ............... A61N 1/368 607/4 |
| 2012/0136406 A1 | 5/2012 | Min |
| 2012/0172892 A1 | 7/2012 | Grubac et al. |
| 2013/0035748 A1 | 2/2013 | Bonner et al. |
| 2014/0121720 A1 | 5/2014 | Bonner et al. |
| 2016/0015322 A1 | 1/2016 | Anderson et al. |

OTHER PUBLICATIONS

William J. Combs et al., "Cross-Talk in Bipolar Pacemakers", PACE, Oct. 1989, pp. 1613-1621, vol. 12.

* cited by examiner

PACING CROSSTALK DETECTION

TECHNICAL FIELD

The disclosure relates to an implantable medical device system and associated method for detecting pacing crosstalk between intracardiac pacemakers operating in different locations of a patient's heart.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one medical lead for positioning electrodes in one heart chamber, atrial or ventricular, or a dual chamber pacemaker coupled to two leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are wholly implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular pacing may adequately address some patient conditions, other conditions may require atrial and ventricular pacing, commonly referred to as a dual chamber pacing, in order to maintain a regular heart rhythm.

SUMMARY

In general, the disclosure is directed to implantable medical device (IMD) systems that may include an atrial intracardiac pacemaker and a ventricular intracardiac pacemaker and techniques for detecting pacing crosstalk between the two intracardiac pacemakers. Crosstalk occurs when the one pacemaker senses a pacing pulse delivered by the other pacemaker as an intrinsic event, e.g., when an atrial pacing pulse is sensed by a ventricular intracardiac pacemaker as an R-wave. Crosstalk can cause the pacemaker to fail to deliver a pacing pulse when needed. An intracardiac pacemaker operating in accordance with the techniques disclosed herein detects when a sensed event is a crosstalk event and manages pacing therapy delivery in the presence of the detected crosstalk.

In one example, the disclosure provides an implantable pacemaker comprising a sensing module configured to sense cardiac electrical signals received by a pair of electrodes coupled to the pacemaker, a pulse generator configured to generate and deliver pacing pulses to a heart chamber of a patient via the pair of electrodes, and a control module coupled to the sensing module and the pulse generator. The control module is configured to start a pacing escape interval to control a time that a pacing pulse is delivered by the pulse generator, detect a sensed cardiac electrical signal as a crosstalk event, the crosstalk event being an electrical pulse delivered to the patient by a different medical device than the implantable pacemaker, and withhold restarting the pacing escape interval in response to sensing the cardiac electrical signal based on detecting the sensed cardiac electrical signal as the crosstalk event.

In another example, the disclosure provides a method performed by an implantable pacemaker comprising sensing a cardiac electrical signal received by a pair of electrodes coupled to the pacemaker, starting a pacing escape interval by a control module of the implantable pacemaker to control a time that a pacing pulse is delivered in a heart chamber of a patient, detecting the sensed cardiac electrical signal as a crosstalk event, the crosstalk event being an electrical pulse delivered to the patient by a different medical device than the implantable pacemaker, and withholding restarting the pacing escape interval in response to sensing the cardiac electrical signal based on detecting the sensed cardiac electrical signal as the crosstalk event.

In yet another example, the disclosure provides a non-transitory, computer-readable storage medium comprising a set of instructions which, when executed by a control module of an implantable pacemaker, cause the pacemaker to sense a cardiac electrical signal received by a pair of electrodes coupled to the pacemaker, start a pacing escape interval by a control module of the implantable pacemaker to control a time that a pacing pulse is delivered to a heart chamber of a patient, detect the sensed cardiac electrical signal as a crosstalk event, the crosstalk event being an electrical pulse delivered to the patient by a different medical device than the implantable pacemaker, and withhold restarting the pacing escape interval in response to sensing the cardiac electrical signal based on detecting the sensed cardiac electrical signal as the crosstalk event.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below

DETAILED DESCRIPTION

An implantable medical device (IMD) system is disclosed herein that includes two or more intracardiac pacemakers each configured to be implanted wholly in a chamber of the patient's heart. In various examples, the IMD system includes an atrial intracardiac pacemaker and a ventricular intracardiac pacemaker that do not require transvenous leads but are enabled to provide coordinated atrial and ventricular pacing without requiring wireless or wired communication signals between the two intracardiac pacemakers on a beatto-beat basis. An intracardiac pacemaker included in the system includes a control module that monitors sensed events for detecting sensed events that are pacing crosstalk events and responds to the crosstalk event detection to properly manage pacing pulse delivery in the presence of pacing crosstalk.

In past practice, a dual chamber pacemaker positioned in an implant pocket and coupled to transvenous atrial and ventricular leads may be programmed to deliver only atrial pacing (AAI(R)), only ventricular pacing (VVI(R)) or both (DDD(R)) according to patient need. The dual chamber pacemaker is able to control the delivery of pacing pulses in both atrial and ventricular chambers because the pacemaker will receive cardiac event signals from both atrial and ventricular chambers via correspondingly placed sensing electrodes and control when a pacing pulse is delivered in both chambers relative to the sensed events using the electrodes positioned in both chambers. In other words, the dual chamber pacemaker "knows" when both sensed and paced events have occurred in both atrial and ventricular pacing channels since all sensing and pacing control is happening in the one device, i.e., the dual chamber pacemaker.

Intracardiac pacemakers adapted to be implanted wholly within a heart chamber eliminate the need for transvenous, intracardiac leads. Complications due to infection associated with a lead extending from a subcutaneous pacemaker pocket transvenously into the heart can be eliminated. Other complications such as "Twiddler's syndrome", lead fracture or poor connection of the lead to the pacemaker are eliminated in the use of an intracardiac pacemaker. Since the sensing and pacing functions in two different heart chambers are being controlled by two different devices that are not in wired communication with each other, pacing crosstalk can occur. Wireless communication between two intracardiac pacemakers may be minimized to conserve power and increase battery longevity. As such, one intracardiac pacemaker does not receive a direct signal through wired or wireless communication indicating when another pacemaker in another heart chamber or at another heart location is delivering a pacing pulse. If a pacing pulse delivered by another pacemaker is sensed as an intrinsic depolarization, pacing therapy needed by the patient may be withheld.

Figure 1:
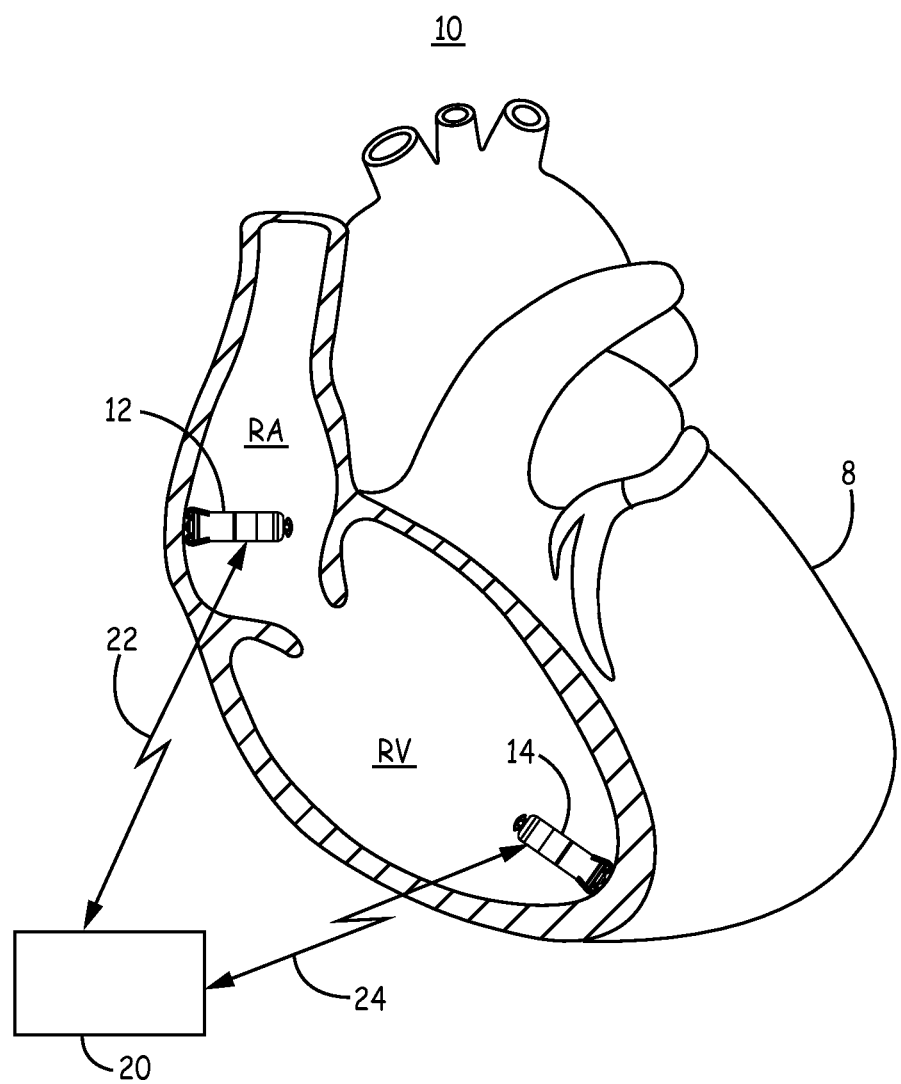
FIG. 1 is a conceptual diagram illustrating an intracardiac pacing system that may be used to sense cardiac electrical signals and provide therapy to a patient's heart.

FIG. 1 is a conceptual diagram illustrating an intracardiac pacing system 10 that may be used to sense cardiac electrical signals and provide therapy to a patient's heart 8. IMD system 10 includes a right atrial (RA) intracardiac pacemaker 12 and a right ventricular (RV) intracardiac pacemaker 14. Pacemakers 12 and 14 are transcatheter intracardiac pacemakers adapted for implantation wholly within a heart chamber, e.g., wholly within the RV, wholly within the left ventricle (LV), wholly within the RA or wholly within the left atrium (LA) of heart 8. In the example of FIG. 1, pacemaker 12 is positioned along an endocardial wall of the RA, e.g., along the RA lateral wall or RA septum. Pacemaker 14 is positioned along an endocardial wall of the RV, e.g., near the RV apex. The techniques disclosed herein, however, are not limited to the pacemaker locations shown in the example of FIG. 1 and other positions and relative locations from each other are possible. In some examples, a RA intracardiac pacemaker 12 and an LV intracardiac pacemaker (not illustrated in FIG. 1) are implanted for delivering pacing therapy. In other examples, a RA pacemaker 12, RV pacemaker 14 and LV pacemaker may be provided. The techniques disclosed herein are relevant to IMD systems including at least two pacemakers each configured to sense and pace in different heart chambers or at different heart locations.

Pacemakers 12 and 14 are reduced in size and may be generally cylindrical in shape to enable transvenous implantation via a delivery catheter. In other examples, pacemakers 12 and 14 may be positioned at any other location inside or outside heart 8, including epicardial locations. For example, pacemaker 12 may be positioned outside or within the right atrium or left atrium to provide respective right atrial or left atrial pacing. Pacemaker 14 may be positioned outside or within the right ventricle or left ventricle to provide respective right ventricular or left ventricular pacing.

Pacemakers 12 and 14 are each capable of producing electrical stimulation pulses, i.e., pacing pulses, delivered to heart 8 via one or more electrodes on the outer housing of the pacemaker. RA pacemaker 12 is configured to sense an intracardiac electrogram (EGM) signal in the RA using the housing based electrodes and deliver RA pacing pulses. RV pacemaker 14 is configured to sense an EGM signal in the RV using one or more housing based electrodes and deliver RV pacing pulses.

The RA pacemaker 12 and the RV pacemaker 14 are configured to control the delivery of pacing pulses to the respective atrial and ventricular chambers in a manner that promotes coordinated dual chamber pacing. Examples of dual chamber pacing therapy delivered by separate atrial and ventricular intracardiac pacemakers are generally disclosed in commonly-assigned U.S. Pat. App. Publication No. 2014/0121720 (Bonner, et al.), incorporated herein by reference in its entirety.

Pacemaker 12 and 14 are each capable of bidirectional wireless communication with an external device 20. External device 20 may be a programmer used by a clinician or other user in a medical facility, a home monitor located in a patient's home, or a handheld device. Aspects of external device 20 may generally correspond to the external programming/monitoring unit disclosed in U.S. Pat. No. 5,507,782 (Kieval, et al.), hereby incorporated herein by reference in its entirety.

External device 20 may be configured to establish a wireless radio frequency (RF) communication link 22 with RA pacemaker 12 and wireless RF communication link 24 with RV pacemaker 14. An example RF telemetry communication system that may be implemented in system 10 is generally disclosed in U.S. Pat. No. 5,683,432 (Goedeke, et al.), hereby incorporated herein by reference in its entirety. Communication links 22 and 24 may be established using a radio frequency (RF) link, for example in the Medical Implant Communication Service (MICS) band, Medical Data Service (MEDS) band, BLUETOOTH® or Wi-Fi.

External device 20 may be capable of bi-directional communication with pacemakers 12 and 14 over a wide range of distances, e.g., up to approximately 10 meters. In other examples, telemetry communication may require the use of a programming head placed in proximity of the patient, e.g. against or within several centimeters of the patient's skin or clothing, to facilitate data transfer.

It is contemplated that external device 20 may be in wired or wireless connection to a communications for transferring data to a remote database or computer to allow remote management of the patient. An example communication scheme that may be used for remotely programming IMD system 10 using the techniques disclosed herein is generally disclosed in U.S. Pat. No. 6,442,433 (Linberg), incorporated herein by reference in their entirety.

External device 20 may be used for retrieving data from pacemakers 12 and 14 and for sending data to pacemakers 12 and 14. Examples of retrieved data include physiological signals such as RA or RV EGM signals, therapy delivery data such as a history of pacing frequency, results of device diagnostic testing, current operating control parameters or other data stored by the pacemaker. Data sent to pacemakers 12 and 14 may include programmable control parameters used by the pacemakers 12 and 14 to control sensing and pacing functions.

RA pacemaker 12 and RV pacemaker 14 may or may not be configured to communicate directly with each other. For example, neither RA pacemaker 12 nor RV pacemaker 14 may be configured to initiate an RF communication session with the other device. Both pacemakers 12, 14 may be configured to periodically "listen" for a valid "wake up" telemetry signal from external device 20 and power up its own telemetry module to establish a communication link 22 or 24 in response to a valid RF telemetry signal (or go back to "sleep" if no valid telemetry signal is received). However, pacemakers 12 and 14 may not be configured to transmit a "wake up" signal to the other pacemaker to initiate a communication session. In other examples, the pacemakers 12 and 14 may be configured to communicate with each other, but, in order to conserve battery life of the intracardiac pacemakers, telemetry communication may be minimized. As such, communication does not occur on a beat-by-beat basis between the RA pacemaker 12 and RV pacemaker 14 for communicating when the other pacemaker is sensing cardiac events or when it is delivering pacing pulses.

In accordance with techniques disclosed herein, RA pacemaker 12 may be configured to sense events from the RA EGM signal and detect sensed events that are ventricular pacing pulses delivered by RV pacemaker as crosstalk events to avoid false sensing of the ventricular pacing pulses as P-waves. RV pacemaker 14 is configured to sense events from the RV EGM signal and detect sensed events that are atrial pacing pulses delivered by RA pacemaker 12 as crosstalk events to avoid false sensing of the atrial pacing pulses as R-waves.

Figure 2A:
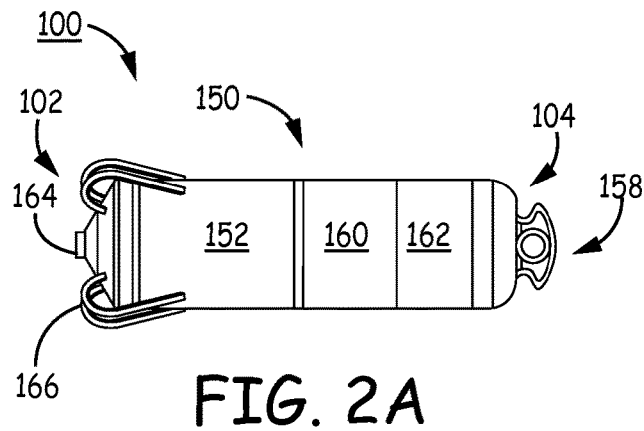
FIGS. 2A-2C are conceptual diagrams of an intracardiac pacemaker that may correspond to the pacemakers shown in FIG. 1.

FIG. 2A is a conceptual diagram of an intracardiac pacemaker 100 that may correspond to RA pacemaker 12 or RV pacemaker 14 shown in FIG. 1. Pacemaker 100 includes electrodes 162 and 164 spaced apart along the housing 150 of pacemaker 100 for sensing cardiac EGM signals and delivering pacing pulses. Electrode 164 is shown as a tip electrode extending from a distal end 102 of pacemaker 100, and electrode 162 is shown as a ring electrode along a mid-portion of housing 150, for example adjacent proximal end 104. Distal end 102 is referred to as "distal" in that it is expected to be the leading end as it advanced through a delivery tool, such as a catheter, and placed against a target pacing site.

Electrodes 162 and 164 form an anode and cathode pair for bipolar cardiac pacing and sensing. Electrodes 162 and 164 may be positioned on or as near as possible to respective proximal and distal ends 104 and 102 to increase the inter-electrode spacing between electrodes 162 and 164. Relatively greater inter-electrode spacing will increase the likelihood of sensing FF signals that may be used by the pacemaker 100 for sensing events in another heart chamber. For example, an increased inter-electrode spacing between electrodes 162 and 164 when pacemaker 100 is used as an RV pacemaker 14 may improve reliable sensing of FF P-waves.

In alternative embodiments, pacemaker 100 may include two or more ring electrodes, two tip electrodes, and/or other types of electrodes exposed along pacemaker housing 150 for delivering electrical stimulation to heart 8 and sensing EGM signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 100 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150 may function as an electrode instead of providing a localized electrode such as electrode 162. Alternatively, electrode 162 may be electrically isolated from the other portions of the housing 150.

The housing 150 includes a control electronics subassembly 152, which houses the electronics for sensing cardiac signals, producing pacing pulses and controlling therapy delivery and other functions of pacemaker 100. Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 100 may include a set of fixation tines 166 to secure pacemaker 100 to patient tissue, e.g., by interacting with the ventricular trabeculae. Fixation tines 166 are configured to anchor pacemaker 100 to position electrode 164 in operative proximity to a targeted tissue for delivering therapeutic electrical stimulation pulses. Numerous types of active and/or passive fixation members may be employed for anchoring or stabilizing pacemaker 100 in an implant position. Pacemaker 100 may include a set of active fixation tines as disclosed in commonly-assigned, pre-grant publication U.S. 2012/0172892 (Grubac, et al.), hereby incorporated herein by reference in its entirety.

Pacemaker 100 may further include a delivery tool interface 158. Delivery tool interface 158 is located at the proximal end 104 of pacemaker 100 and is configured to connect to a delivery device, such as a catheter, used to position pacemaker 100 at an implant location during an implantation procedure, for example within a heart chamber.

A reduced size of pacemaker 100 enables implantation wholly within a heart chamber. In FIG. 1, RA pacemaker 12 and RV pacemaker 14 may have different dimensions. For example, RA pacemaker 12 may be smaller in volume than pacemaker 14, e.g., by reducing battery size, to accommodate implantation in the smaller heart chamber. As such, it is recognized that pacemaker 100 may be adapted in size, shape, electrode location or other physical characteristics according to the heart chamber in which it will be implanted.

Figure 2B:
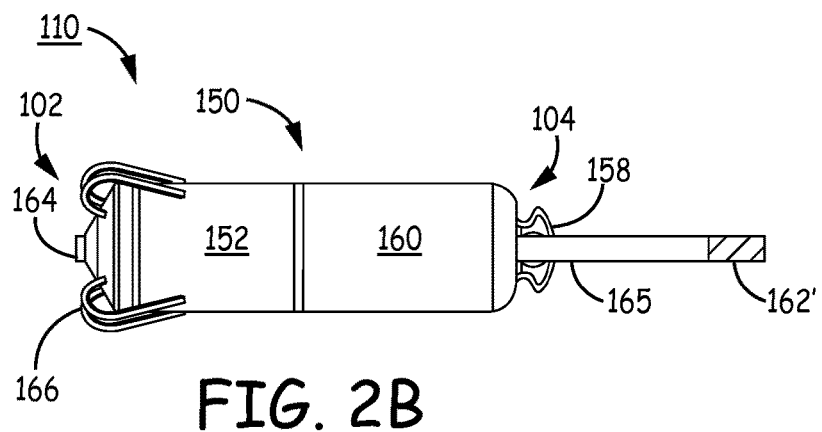

FIG. 2B is a conceptual diagram of an alternative embodiment of an intracardiac pacemaker 110. Pacemaker 110 includes a housing 150, control assembly 152, battery assembly 160, fixation member 166 and electrode 164 along a distal end 102, and may include a delivery tool interface 158 along the proximal end 104 as described above in conjunction with FIG. 2A. Pacemaker 110 is shown to include an electrode 162' extending away from housing 150 along an extender 165. As such, instead of carrying a pair of electrodes along the housing 150, which limits the maximum possible inter-electrode spacing, an extender 165 may be electrically coupled to the housing 150 for positioning an electrode 162' at an increased inter-electrode distance from distal tip electrode 164, in which case all or a portion of housing 150 may be insulated.

For examples of an intracardiac pacemaker having increased inter-electrode spacing between electrodes, reference is made to commonly-assigned, pre-grant U.S. Publication No. (Bonner, et al.) and U.S. Patent Application Ser. No. 62/025,690, filed on Jul. 17, 2014, both of which are incorporated herein by reference their entirety.

Figure 2C:
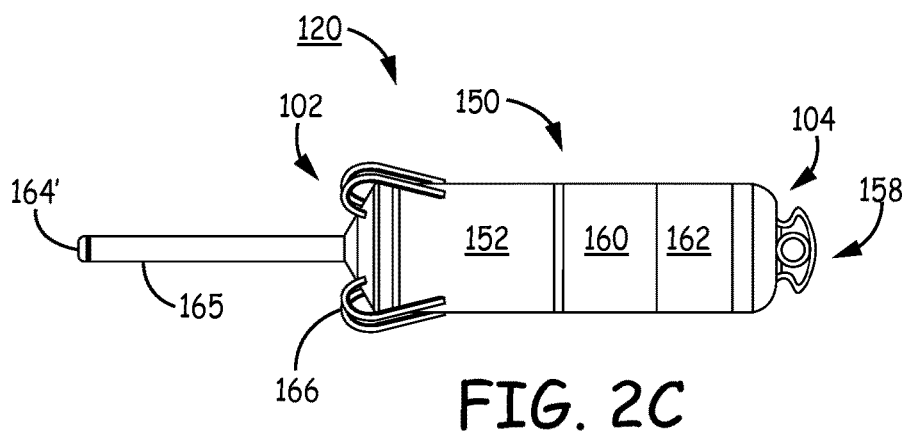

FIG. 2C is a conceptual diagram of an alternative embodiment of intracardiac pacemaker 120 having extender 165 coupled to the distal end 102 of pacemaker housing 150 to extend distal electrode 164' away from electrode 162 positioned along housing 150 near or at proximal end 104. Extender 165 shown in FIGS. 2B and 2C is an insulated electrical conductor that electrically couples electrode 162' (FIG. 2B) or electrode 164' (FIG. 2C) to pacemaker circuitry via an electrical feedthrough crossing housing 150. Pacemaker 120 having an insulated, electrically conductive extender 165 for increasing the inter-electrode spacing may correspond generally to the implantable device and flexible conductor disclosed in the above incorporated U.S. Publication No. 2013/0035748 (Bonner, et al.).

Figure 3:
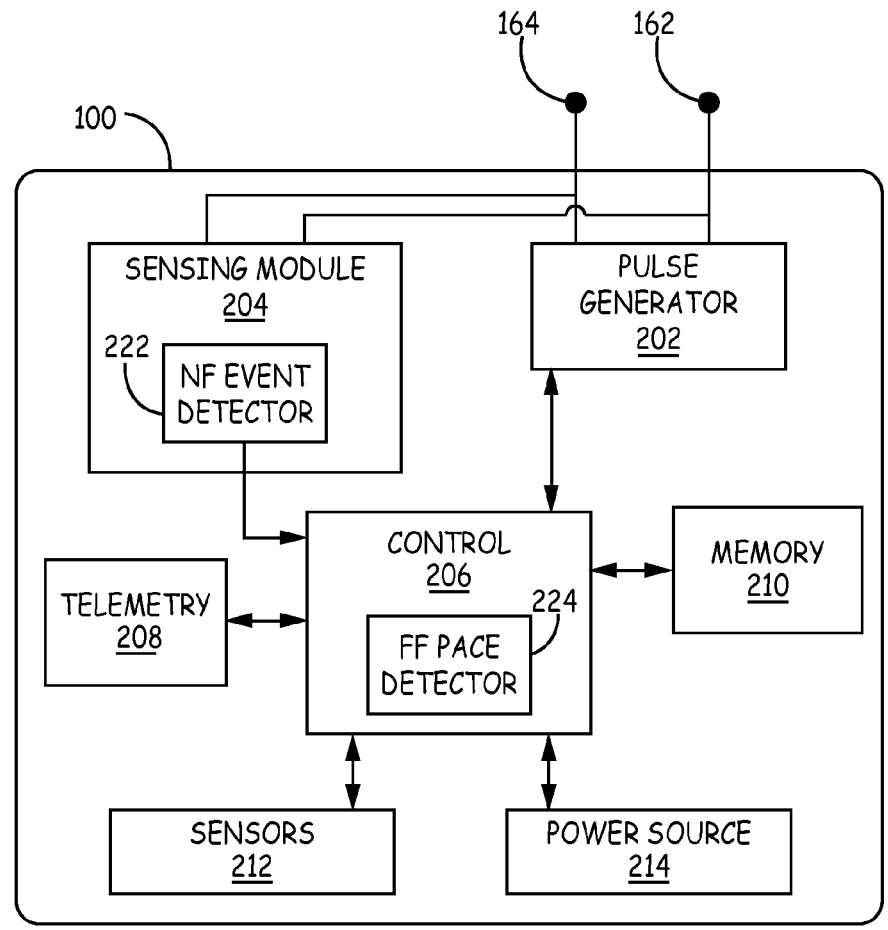
FIG. 3 is a functional block diagram of an example configuration of the pacemakers shown in FIG. 2A, 2B or 2C.

FIG. 3 is a functional block diagram of an example configuration of pacemaker 100 shown in FIG. 2A. Pacemaker 100 includes a pulse generator 202, a sensing module 204, a control module 206, memory 210, telemetry module 208 and a power source 214. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. Each of RA pacemaker 12 and RV pacemaker 14 will include similar modules as represented by the pacemaker 100 shown in FIG. 3; however it is understood that the modules are configured differently as needed to perform the functionality of the separate RA and RV pacemakers 12 and 14 as disclosed herein.

For example, when pacemaker 100 is a RA pacemaker 12, control module 206 is configured to set various atrial pacing escape intervals used to control delivery of atrial pacing pulses as disclosed herein. When pacemaker 100 is embodied as RV pacemaker 14, control module 206 is configured to set ventricular pacing escape intervals to control delivery of RV pacing pulses according to techniques disclosed herein. Adaptations of the hardware, firmware or software of the various modules of pacemaker 100 necessary to meet the described functionality of the intracardiac pacemakers positioned in different heart chambers as disclosed herein is understood to be included in the various modules of pacemaker 100 according to the intended implant location.

The functions attributed to pacemaker 100 herein may be embodied as one or more processors, controllers, hardware, firmware, software, or any combination thereof. Depiction of different features as specific circuitry or modules is intended to highlight different functional aspects and does not necessarily imply that such functions must be realized by separate hardware or software components or by any particular architecture. Rather, functionality associated with one or more modules, processors, or circuits may be performed by separate hardware or software components, or integrated within common hardware or software components. For example, pacing control operations performed by pacemaker 100 may be implemented in control module 206 executing instructions stored in associated memory 210 and relying on input from sensing module 204.

Pulse generator 202 generates electrical stimulation pulses that are delivered to heart tissue via electrodes 162 and 164. Electrodes 162 and 164 may be housing-based electrodes as shown in FIG. 2A, but one or both electrodes 162 and 164 may alternatively be carried by an insulated, electrical conductor extending away from the pacemaker housing as described in conjunction with FIGS. 2B and 2C.

Pulse generator 202 may include one or more capacitors and a charging circuit to charge the capacitor(s) to a programmed pacing pulse voltage. At appropriate times, e.g., as controlled by a pacing escape interval timer included in a pace timing and control circuit in control module 206, the capacitor is coupled to pacing electrodes 162 and 164 to discharge the capacitor voltage and thereby deliver the pacing pulse. Pacing circuitry generally disclosed in the above-incorporated U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 100 for charging a pacing capacitor to a predetermined pacing pulse amplitude under the control of control module 206 and delivering a pacing pulse.

Control module 206 controls pulse generator 202 to deliver a pacing pulse in response to expiration of a pacing escape interval according to programmed therapy control parameters stored in memory 210. Control module 206 may include an escape interval timer or counter that is set to various pacing escape intervals used for controlling the timing of pacing pulses relative to a paced or sensed event. Upon expiration of a pacing escape interval, a pacing pulse is delivered. If a cardiac event is sensed during the pacing escape interval by sensing module 204, the scheduled pacing pulse may be inhibited, and the pacing escape interval may be reset to a new escape interval.

Sensing module 204 receives a cardiac EGM signal developed across electrodes 162 and 164. Sensing module 204 may include a bandpass filter, which may be an adjustable filter, that has a center frequency and passband selected to filter non-cardiac signals and improve the signal-to-noise ratio for sensing intrinsic cardiac events.

Sensing module 204 may include a near-field (NF) event detector 222. A cardiac event is sensed by sensing module 204 when the EGM signal crosses a sensing threshold of the cardiac event detector 222 in some examples. The sensing threshold may be an auto-adjusting sensing threshold that may be initially set based on the amplitude of a sensed event and decays at a predetermined decay rate thereafter.

NF cardiac events are events that occur in the heart chamber where the electrodes 162 and 164 are located. The NF cardiac event detector 222 of RA pacemaker 12 may be programmed or configured to operate using a sensing threshold appropriate for sensing intrinsic P-waves attendant to the depolarization of the atria. The NF cardiac event detector 222 of RV pacemaker 14 may be programmed or configured to operate using a sensing threshold appropriate for sensing intrinsic R-waves attendant to the depolarization of the ventricles. NF cardiac event detector 222 produces a sensed event signal provided to control module 206 in response to sensing a NF event, i.e., a P-wave by RA pacemaker 12 or an R-wave by RV pacemaker 14. The NF event may be sensed based on a sensing threshold crossing. The sensed event signal may be used by control module 206 to reset a pacing escape interval used to control the timing of pacing pulses when the pacemaker 100 is operating in an inhibiting pacing mode, such as a VVI pacing mode.

Sensing module 204 may include a digital convertor that converts the EGM signal received across electrodes 162 and 164 to a multi-bit digital signal. Control module 206 may receive the multi-bit digital signal from electrical sensing module 204 and analyze the digital signal for use in detecting cardiac events and controlling pulse generator 202 to deliver appropriate therapy. Control module 206 may include FF pace detector 224 for detecting crosstalk events due to electrical stimulation pulses delivered by another device present in the patient. FF pace events are pacing pulses delivered by a different pacemaker to a different location than the location where electrodes 162 and 164 are located. For example, FF pace events may be detected when pacing pulses are delivered in a different heart chamber than the chamber that pacemaker 100 is implanted in. In some cases, more than one pacemaker may be implanted along a single heart chamber in which case one pacemaker may detect crosstalk events that are pacing pulses or other electrical pulses delivered to a different location of the heart chamber by a different pacemaker. In general, FF pace detector 224 may be configured to detect electrical stimulation pulses delivered to the patient by a medical device that is not pacemaker 100.

FF pace detector 224 may be configured to detect FF pacing pulses and may produce a FF pace event signal used by control module 206 to control the pacing escape interval timer. FF ventricular pacing pulses may be detected by FF event detector 224 in RA pacemaker 12. FF atrial pacing pulses may be detected by FF pace detector 224 in RV pacemaker 14.

Memory 210 may include computer-readable instructions that, when executed by control module 206, cause control module 206 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 may store timing intervals, counters, or other data used by control module 206 to control the delivery of pacing pulses by pulse generator 202, e.g., by setting a pacing escape interval timer included in control module 206, according to the techniques disclosed herein.

Pacemaker 100 may further include one or more physiological sensors 212 used for monitoring the patient. In some examples, physiological sensors 212 include at least one physiological sensor producing a signal indicative of the metabolic demand of the patient. The signal indicative of the patient's metabolic demand is used by control module 206 for determining a sensor indicated pacing rate to control a pacing rate that meets the patient's metabolic demand. For example, sensors 212 may include an accelerometer for producing a patient activity signal passed to control module 206.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries. The connections between power source 214 and other pacemaker modules and components are not shown in FIG. 3 for the sake of clarity.

Telemetry module 208 includes a transceiver and associated antenna for transferring and receiving data via a radio frequency (RF) communication link as described above. RF communication with external device 20 (FIG. 1), may occur in the Medical Implant Communication Service (MICS) band, the Medical Data Service (MEDS) band, or other frequency bands, including, but not limited to a 2.4 GHz industrial, scientific and medical (ISM) band for Bluetooth and IEEE 802.11 b/g/n standards.

Figure 4:
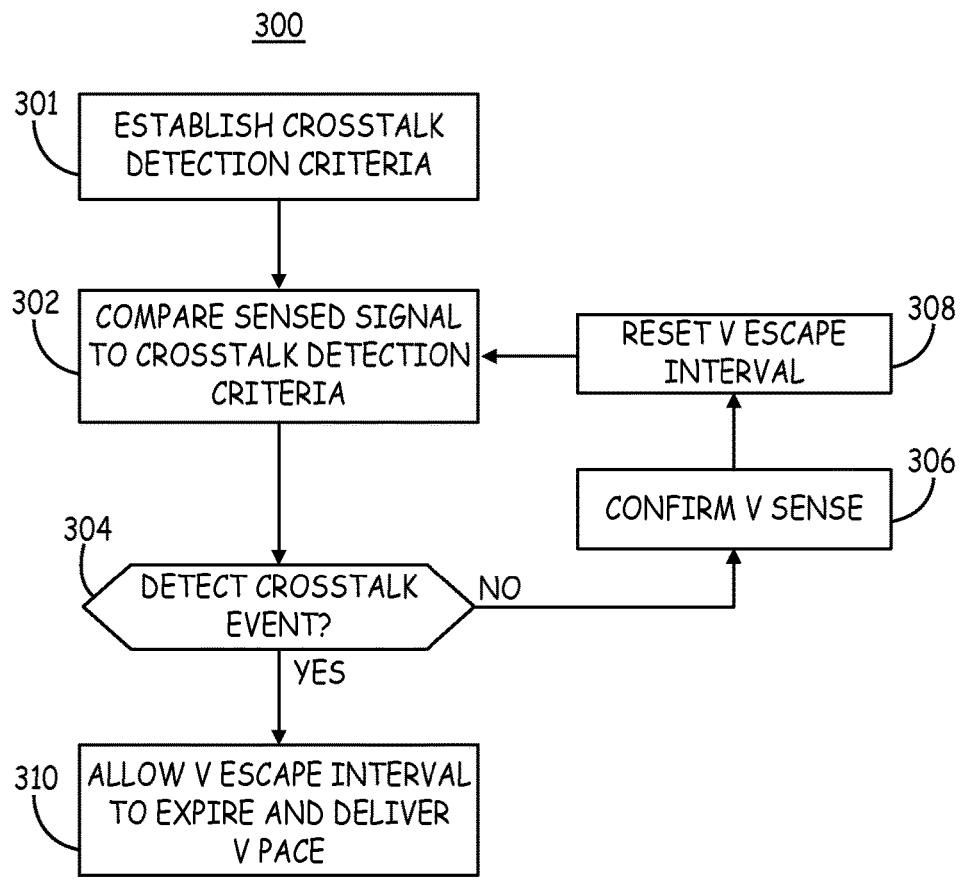
FIG. 4 is a flow chart of a method for controlling pacing pulse delivery by the pacemaker shown in FIG. 3.

FIG. 4 is a flow chart 300 of a method for controlling pacing pulse delivery by pacemaker 100. Flow chart 300 and other flow charts presented herein are intended to illustrate the functional operation of the device, and should not be construed as reflective of a specific form of software or hardware necessary to practice the methods described. It is believed that the particular form of software, hardware and/or firmware will be determined primarily by the particular system architecture employed in the pacemaker 100 and by the particular detection and therapy delivery methodologies employed by the pacemaker 100. Providing software, hardware, and/or firmware to accomplish the described functionality in the context of any modern pacemaker system, given the disclosure herein, is within the abilities of one of skill in the art. Methods described in conjunction with flow charts presented herein may be implemented in a computer-readable medium that includes instructions for causing a programmable processor to carry out the methods described. The instructions may be implemented as one or more software modules, which may be executed by themselves or in combination with other software.

The flow chart 300 is described here in the context of RV pacemaker 14 managing ventricular pacing pulse delivery in the presence of atrial pacing pulses delivered by RA pacemaker 12. Atrial pacing pulses delivered by RA pacemaker 12 may be falsely sensed as R-waves by RV pacemaker 14. These falsely sensed R-waves that are actually atrial pacing pulses are referred to herein as crosstalk events. It is recognized that techniques described herein relating to RV pacemaker 14 and managing pacing pulse delivery in the presence of atrial pacing pulses delivered by RA pacemaker 12 may be adapted for use when pacemaker 100 is positioned in the RA, LA, RV or LV when another device is implanted for delivering pacing pulses to any other heart chamber, or more generally when another medical device is implanted for delivering electrical stimulation pulses to the patient that may be sensed by the pacemaker 100.

At block 301, crosstalk detection criteria are established. Crosstalk detection criteria may be programmable parameters entered by a user or set to default values and stored in memory 210 for use by control module 206. Alternatively crosstalk detection criteria may be established automatically by control module 206 during known crosstalk conditions, e.g., during confirmed atrial pacing. For example, RA pacemaker 12 may be programmed by a clinician to deliver atrial pacing pulses at a rate greater than the patient's intrinsic heart rate at a pulse amplitude and pulse width expected to be used for atrial pacing. A user command to establish crosstalk detection criteria may be transmitted to RV pacemaker 14 by external device 20.

Sensing module 204 may sense a series of events which include true R-waves and crosstalk events and pass a sensed event signal to control module 206 upon each sensed event. Upon receiving the command to establish crosstalk detection criteria, FF pace detector 224 may determine which of the sensed event signals from sensing module are crosstalk events and which are true sensed R-waves based on timing and/or signal morphology. For example, a crosstalk event may cross an R-wave sensing threshold but have an overall lower peak amplitude and/or narrower signal width. Crosstalk events may be identified from among the sensed event signals by using another physiological signal of mechanical heart activity, such as heart sounds or blood pressure to eliminate sensed event signals that are correlated in time to ventricular mechanical systole. A crosstalk event may additionally or alternatively be identified by delivering ventricular pacing pulses at a safety pace interval following a sensed event signal and verifying capture of the ventricle following the ventricular pacing pulse (as described below).

Once crosstalk events are identified, one or more features of identified crosstalk events may be determined, e.g., peak amplitude, signal width, peak slope, signal area, etc., and crosstalk detection thresholds may be set based on each respective feature value that distinguish the crosstalk event from a true sensed R-wave. Additionally or alternatively, a crosstalk signal morphology template may be established, e.g., by averaging multiple verified crosstalk signals.

In some examples, an EGM signal during the known crosstalk condition may be retrieved from RV pacemaker 14 by external device 20, and a user may manually select which sensed events are crosstalk events. The external device 20 may determine crosstalk detection criteria from the selected signals and transmit the crosstalk detection criteria back to RV pacemaker 14.

After establishing crosstalk detection criteria, RV pacemaker 14 begins normal operation. At block 302, a signal sensed as a cardiac event from the EGM signal received by sensing module 204 is analyzed by FF pace detector 224 to determine whether the sensed event is a crosstalk event, i.e., a FF pacing pulse. In some examples, FF pace detector 224 evaluates the EGM signal over an analysis window set in response to a sensed event signal received from sensing module 204. Sensing module 204 may pass a sensed event signal to control module 206 in response to sensing an R-wave from the EGM signal based on an R-wave sensing threshold crossing by the EGM signal. FF pace detector 224 may analyze the amplitude, width, signal area, slope, shape or other morphology feature of the EGM signal around the time of the sensed event signal. One or more signal morphology features and/or a correlation between the EGM signal and a crosstalk template is/are compared to crosstalk detection criteria at block 302. The crosstalk detection criteria may include one or more detection thresholds applied to respective features of the EGM signal and/or a correlation threshold applied to a correlation determined between the EGM signal and a crosstalk signal template previously established under a known crosstalk condition at block 301.

If the crosstalk detection criteria are not met, the sensed event signal is confirmed to be a sensed ventricular (V) event, i.e., an R-wave, at block 306. The ventricular pacing escape interval timer is reset at block 308 in response to sensing the R-wave according to normal pacing operation in an inhibiting pacing mode such as a VVI pacing mode.

If the cross-talk detection criteria are met at block 304, the sensed event signal produced by sensing module 204 is not used by control module 206 to reset the ventricular pacing escape interval. The ventricular pacing escape interval is allowed to continue and may expire at block 310. Upon expiration, the scheduled ventricular pacing pulse is delivered at block 310. During normal operation in an inhibiting pacing mode, a sensed event signal produced by NF event detector 222 causes control module 206 to inhibit a scheduled pacing pulse by causing the pacing escape interval to be reset. Control module 206 withholds restarting the pacing escape interval in response to sensing a cardiac electrical signal that is detected as a crosstalk event by FF pace detector 224, even though NF event detector 222 may produce a sensed event signal in response to the EGM signal crossing a sensing threshold or meeting other sensing criteria.

Figure 5:
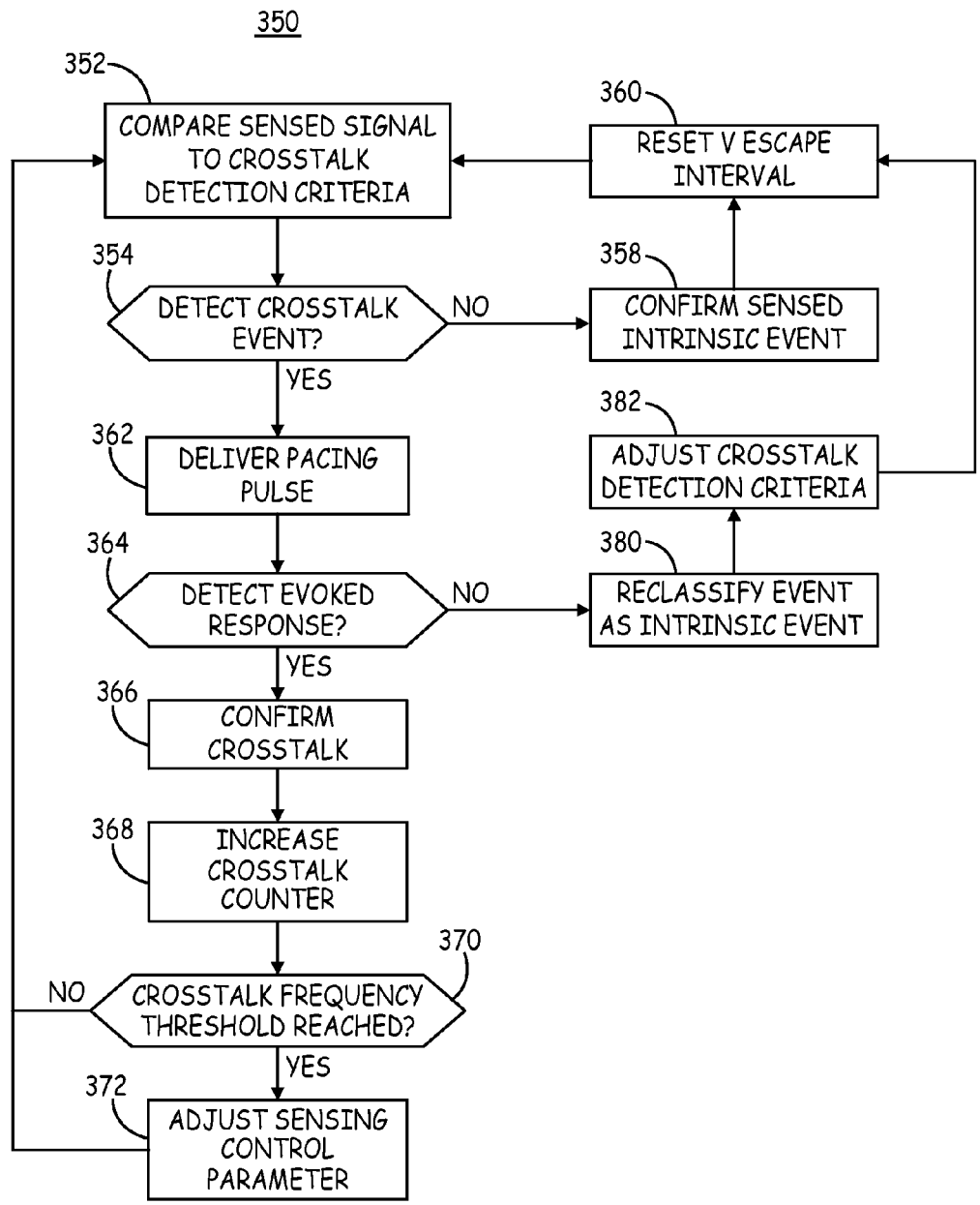
FIG. 5 is a flow chart of a method for detecting crosstalk and controlling pacing in the presence of another pacemaker according to another example.

FIG. 5 is a flow chart 350 of a method for detecting crosstalk and controlling pacing in the presence of another pacemaker according to another example. At block 352, control module 206 compares a sensed signal to crosstalk detection criteria. Crosstalk detection criteria may be previously established as described above in conjunction with FIG. 4. The control module 206 may receive the EGM signal from sensing module 204 and compare the EGM signal to a crosstalk detection threshold. A crosstalk detection threshold crossing may result in detection of a crosstalk event at block 354. In another example, the control module 206 may set an EGM signal analysis window in response to receiving a sensed event signal, e.g., an R-wave sensed event signal produced by NF event detector 222. The EGM signal may be analyzed during the window to determine if crosstalk detection criteria are met. Crosstalk detection criteria may include EGM morphology-based criteria, such as, but not limited to, amplitude, signal width, signal area, maximum slope, or waveform shape or correlation to a crosstalk template.

Crosstalk detection criteria may include timing related criteria. For example, control module 206 may determine a sensed event interval between a sensed event signal received from NF event detector 222 and a most recent preceding event, sensed and paced. The sensed event interval may be compared to an expected intrinsic event interval, e.g., a running average RR interval determined from six to ten of the most recent RR intervals. If the sensed event interval is shorter than the expected intrinsic event interval by a predetermined threshold, e.g., less than 25% of the expected event interval, additional morphological analysis of the EGM signal may be performed to determine if the sensed event is a crosstalk event.

If crosstalk detection criteria are not met at block 354, the sensed event is confirmed as an intrinsic event, e.g., an R-wave, at block 358. In some cases, a sensed R-wave may be a PVC that occurs earlier than an expected sensed event interval but does not meet other crosstalk detection criteria. If the crosstalk detection criteria are not met, the pacing escape interval, i.e., a ventricular pacing escape interval in this example, is restarted at block 360 in response to the sensed R-wave.

If crosstalk detection criteria are met, control module 206 controls pulse generator 202 to deliver a pacing pulse at block 362. The pacing pulse may be delivered at a predetermined safety pace interval, e.g., within 70 to 110 ms after the detected crosstalk event. If the sensed event is a true crosstalk event, e.g., an atrial pacing pulse delivered by RA pacemaker 12 and sensed by RV pacemaker 14, delivery of a ventricular pacing pulse at a safety pace interval at block 362 results in a relatively short AV interval but avoids delivering a ventricular pacing pulse upon expiration of a currently running ventricular pacing escape interval, which may result in pacing during a vulnerable period associated with repolarization of the ventricle. The vulnerable period is typically between 200 and 400 ms after the R-wave. If the sensed event is detected as a crosstalk event but is actually an R-wave, e.g., a PVC, the pacing pulse delivered at the safety pace interval will be delivered during ventricular refractory and before the vulnerable period.

At block 364, the control module 206 may determine if an evoked response due to the pacing pulse is detected. If an evoked response is not detected, the sensed event detected as crosstalk was more likely to be a true R-wave and may be reclassified as an intrinsic event at block 380. The sensed event detected as a crosstalk event may be reclassified as a PVC at block 380 if the event was sensed earlier than an expected sensed event interval. At block 382, the control module 206 may adjust the crosstalk detection criteria in response to the crosstalk event being reclassified as a true intrinsic event. For example, a detection threshold, time interval, or other criterion used to detect crosstalk may be adjusted at block 382 so that the sensed event that resulted in crosstalk detection at block 354 does not meet the adjusted criterion.

A pacing escape interval is restarted at block 360 in response to delivering the pacing pulse at the safety pace interval. The pacing escape interval may be set to an adjusted interval based on reclassifying the detected crosstalk event as a true intrinsic event. For example, the pacing escape interval may be set to the currently programmed pacing escape interval less the safety pace interval so that the adjusted pacing escape interval expires at the desired escape interval after the true intrinsic event, as if the pacing escape interval had been started at the time that the true intrinsic event was sensed.

If a pacing evoked response is detected at block 364, the crosstalk event is confirmed at block 366. The sensed event detected as crosstalk is not an intrinsic event because if it was, the pacing pulse would have been delivered during the physiological ventricular refractory period and would not elicit an evoked response. Detection of the evoked response is confirmation that the sensed signal is a crosstalk event. The evoked response may be the electrical evoked response detected from the EGM signal or the mechanical evoked response detected using a sensor of the mechanical heart contraction, such as a pressure sensor, impedance sensor, accelerometer, or acoustical sensor.

The control module 206 may include a crosstalk counter that is increased at block 368 to track the number of times crosstalk events are detected. The crosstalk counter may be reset to zero after a predetermined interval of time, e.g., once per minute, once per hour, once per day or other time interval, such that the crosstalk counter tracks the frequency of crosstalk detections made during the predetermined time interval. If a frequency threshold is not reached before the counter is reset, as determined at block 370, the sensing control parameters remain unchanged and the process returns to block 352 to wait for the next sensed event. To illustrate, a crosstalk frequency threshold may be set, for example, to five crosstalk events in one minute. The counter may be reset to zero after one minute.

If the crosstalk counter reaches a crosstalk frequency threshold at block 370 before the counter is reset, a sensing control parameter may be adjusted at block 372 to reduce the likelihood of sensing crosstalk events. For example, the sensitivity may be decreased (by adjusting a sensitivity control parameter of sensing module 204). In some examples, a sensing threshold decay parameter may be adjusted to decrease the sensitivity. In other example, a bandpass filter included in sensing module 204 may be adjusted to attenuate the FF pacing pulse signal in the sensed EGM signal.

Figure 6:
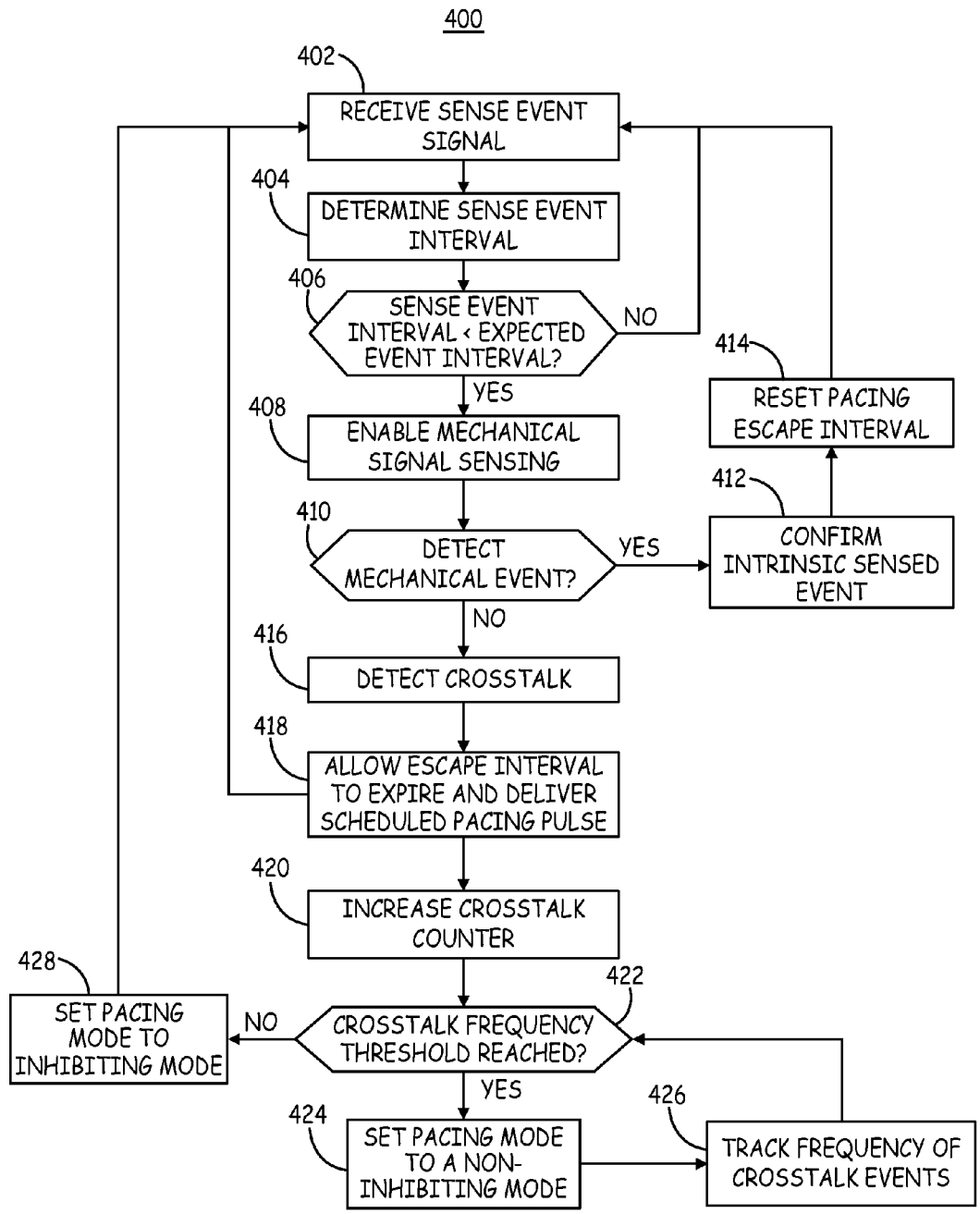
FIG. 6 is a flow chart of method for detecting and responding to crosstalk events according to another example.

FIG. 6 is a flow chart 400 of a method for detecting and responding to crosstalk events according to another example. At block 402, the control module 206 receives a sensed event signal from sensing module 204. At block 404, control module 206 determines a sensed event interval as the time interval from the sensed event signal to an immediately preceding event, sensed or paced. If the sensed event interval is not less than an expected sensed event interval, as determined at block 406, no further action is taken to detect a crosstalk event in some examples.

If the sensed event interval is less than the expected sensed event interval, which may be a running average RR interval as described above, mechanical signal sensing is enabled at block 408. Sensors 212 of pacemaker 100 may include a pressure sensor for producing a blood pressure signal or an acoustical sensor or accelerometer for producing a heart sound signal or heart motion signal. Control module 206 may additionally or alternatively be configured to determine an impedance signal from electrodes 162 and 164 for monitoring dynamic changes in cardiac impedance that occur with changing blood volume over a cardiac cycle. Monitoring of any of these signals may be enabled at block 408 for detecting a mechanical cardiac event associated with systole following the early sensed electrical cardiac event.

If a mechanical event following the early sensed electrical event is detected as evidence of systolic contraction of the ventricles, the early electrical sensed event is confirmed to be a sensed R-wave at block 412. The ventricular pacing escape interval is reset at block 414 based on the timing of the confirmed R-wave sensed event.

If a mechanical event is not detected at block 410, the early sensed electrical event is detected as a crosstalk event at block 416. Control module 206 withholds resetting the pacing escape interval in response to sensing the electrical event based on the crosstalk event detection so that the scheduled pacing pulse is not inhibited due to the crosstalk event. In other words, the sensed electrical event detected as a crosstalk event may be ignored so that the ventricular escape interval is allowed to continue at block 418. If an intrinsic event is not sensed during the escape interval, a pacing pulse may be delivered at the expiration of the escape interval at block 418.

In another example, a pacing pulse may be delivered at a safety pace interval following the detected crosstalk event as described above in conjunction with FIG. 5. In some examples, the decision to deliver a pacing pulse at a safety pace interval after a crosstalk event or to allow a currently running pacing escape interval to expire for delivering a previously scheduled pacing pulse may be based on how early the crosstalk event is detected following the immediately preceding sensed or paced event. For instance, if the detected crosstalk event is less than approximately 250 ms since the last true sensed event or a pacing pulse delivered by RV pacemaker 14, the pacing pulse at the safety pace interval may be withheld to avoid delivering the pacing pulse during the vulnerable period. In another example, if the pacing pulse at the safety pace interval would result in an event interval that is less than a predetermined percentage, e.g., less than 80%, of a running average event interval, the currently running escape interval may be allowed to expire without delivering the pacing pulse at the safety pace interval.

A crosstalk counter may track the number of times crosstalk events are detected at block 420 for triggering adjustment of sensing control parameters as described above, if a threshold frequency of crosstalk detection is reached. In the example of FIG. 6, if a threshold frequency of crosstalk events is reached at block 422, the control module 206 may automatically switch the pacing mode from an inhibiting pacing mode to a non-inhibiting pacing mode in which no sensed events are used to inhibit pacing pulses. For example, if control module 206 of RV pacemaker 14 determines that a threshold frequency of crosstalk events has been detected, the ventricular pacing mode may be switched from a VVI pacing mode to a VOO pacing mode. In the VVI pacing mode, sensed R-waves will inhibit pacing pulses by causing the ventricular escape interval to be reset. Control module 206 will withhold resetting the ventricular escape interval in response to a sensed event that is detected as a crosstalk event. In the VOO pacing mode, pacing pulses are not inhibited due to sensed events; RV pacemaker 14 delivers ventricular pacing pulses at a programmed pacing escape interval that is not reset in response to any sensed events.

At block 424, the pacing mode may be set temporarily to a non-inhibiting pacing mode, e.g., for one minute, one hour, one day or other predefined time interval. The pacing mode may automatically be switched back to an inhibiting pacing mode, e.g., from VOO back to VVI, after the predetermined time interval expires so that sensed events are again used to inhibit pacing pulses. Crosstalk detection may be resumed so that sensed events detected as crosstalk are not used to reset a pacing escape interval during the inhibiting pacing mode.

In another example, the pacing mode may be switched to a non-inhibiting pacing mode in which cardiac event sensing and crosstalk detection remains enabled but all sensed cardiac events are not used to inhibit pacing pulses. For example, the pacing mode may be switched from a VVI mode to a VVO mode in which sensing and crosstalk detection continues while pacing continues at a programmed pacing escape interval without inhibiting pacing pulses due to sensed events. The control module 206 may track the frequency of crosstalk event detection during the non-inhibiting pacing mode at block 426. If the crosstalk detection frequency remains below the frequency threshold at block 422, at the time the crosstalk counter is reset, the pacing mode may be switched back to a sensing and inhibiting mode at block 428, e.g., from the VVO mode to the VVI mode. The inhibiting mode of pacing in which sensed events are used to reset the pacing escape interval is resumed after the frequency of crosstalk detection is determined to decrease to below the crosstalk frequency threshold.

Thus, various examples of a pacemaker configured to detect crosstalk events due to electrical stimulation pulses delivered by another device implanted in the patient and methods for controlling pacing pulse delivery in the presence of crosstalk events have been described. The flowcharts and accompanying description are intended to illustrate various aspects of the crosstalk detection and pacing therapy management that may be implemented in a pacemaker operating according to the disclosed techniques. It is recognized that the steps included in the various flowcharts presented herein may be combined in a different order and/or combination than the particular order and combinations described in the illustrative examples presented. It is recognized that various modifications may be made to the described embodiments without departing from the scope of the following claims.

The invention claimed is:

1. An implantable pacemaker, comprising:
a sensing module configured to sense cardiac electrical signals received by a pair of electrodes coupled to the pacemaker,
a pulse generator configured to generate and deliver pacing pulses to a heart chamber of a patient via the pair of electrodes, and
a control module coupled to the sensing module and the pulse generator and configured to:
start a pacing escape interval to control a time that a pacing pulse is delivered by the pulse generator;
detect a sensed cardiac electrical signal as a crosstalk event, the crosstalk event being an electrical pulse delivered to the patient by a different medical device than the implantable pacemaker,
withhold restarting the pacing escape interval in response to sensing the cardiac electrical signal based on detecting the sensed cardiac electrical signal as the crosstalk event; wherein detecting the crosstalk event comprises:
determining a sensed event interval from the sensed cardiac electrical signal to a preceding cardiac event;
comparing the sensed event interval to an expected cardiac event interval; and
determining if crosstalk detection criteria are met if the sensed event interval is less than the expected cardiac event interval.

2. The pacemaker of claim 1, wherein the control module is configured to detect the sensed cardiac electrical signal as a crosstalk signal by comparing the sensed cardiac electrical signal to at least one crosstalk detection criterion.

3. The pacemaker of claim 1, further comprising a sensor producing a signal comprising mechanical cardiac events, the control module configured to detect the crosstalk event by:
determining from the sensor signal whether a mechanical cardiac event is absent following the sensed cardiac electrical signal, and
detecting the crosstalk signal in response to determining that the mechanical cardiac event is absent following the sensed cardiac electrical signal.

4. The pacemaker of claim 1, wherein the control module is further configured to:
control the pulse generator to deliver a pacing pulse at a safety pace interval following the detected crosstalk event; and
restart the pacing escape interval in response to delivering the pacing pulse.

5. The pacemaker of claim 4, wherein the control module is further configured to:
detect an evoked response following the pacing pulse;
confirm the crosstalk event based on detecting the evoked response;
reclassify the detected crosstalk event as an intrinsic event if the evoked response to the pacing pulse is not detected; and
adjust the restarted pacing escape interval by the safety pace interval in response to reclassifying the detected crosstalk event as an intrinsic event.

6. The pacemaker of claim 5, wherein the control module is further configured to adjust a crosstalk detection criterion in response to reclassifying the detected crosstalk event.

7. The pacemaker of claim 1, wherein the control module is further configured to:
increase a count of detected crosstalk events in response to detecting the crosstalk event;
compare the count to a crosstalk frequency threshold; and
adjust a sensing control parameter in response to the count reaching the crosstalk frequency threshold.

8. The pacemaker of claim 1, wherein the control module is further configured to:

determine an event interval from a preceding event to the detected crosstalk event;
compare the determined event interval to a threshold interval; and
deliver a safety pacing pulse at a safety pace interval if the event interval is greater than the threshold interval.

9. The pacemaker of claim 1, wherein the control module is further configured to switch a pacing mode of the implantable pacemaker from an inhibiting mode to a non-inhibiting mode in response to detecting the crosstalk event.

10. A method performed by an implantable pacemaker, the pacemaker comprising:
sensing a cardiac electrical signal received by a pair of electrodes coupled to the pacemaker,
starting a pacing escape interval by a control module of the implantable pacemaker to control a time that a pacing pulse is delivered in a heart chamber of a patient;
detecting the sensed cardiac electrical signal as a crosstalk event, the crosstalk event being an electrical pulse delivered to the patient by a different medical device than the implantable pacemaker, and
withholding restarting the pacing escape interval in response to sensing the cardiac electrical signal based on detecting the sensed cardiac electrical signal as the crosstalk event;
wherein detecting the crosstalk event comprises:
determining a sensed event interval from the sensed cardiac electrical signal to a preceding cardiac event;
comparing the sensed event interval to an expected cardiac event interval; and
determining if crosstalk detection criteria are met if the sensed event interval is less than the expected cardiac event interval.

11. The method of claim 10, further comprising detecting the sensed cardiac electrical signal as a crosstalk signal by comparing the sensed cardiac electrical signal to at least one crosstalk detection criterion.

12. The method of claim 10, further comprising:
sensing a signal comprising mechanical cardiac events;
detecting the crosstalk event by determining whether a mechanical cardiac event occurs following the sensed cardiac electrical signal and detecting the crosstalk signal in response to not detecting a mechanical cardiac event from the sensor signal following the sensed cardiac electrical signal.

13. The method of claim 10, further comprising:
controlling a pulse generator to deliver a pacing pulse at a safety pace interval following the detected crosstalk event; and
restarting the pacing escape interval upon delivering the pacing pulse.

14. The method of claim 13, further comprising:
detecting an evoked response following the pacing pulse;
confirming the crosstalk event based on detecting the evoked response;
reclassifying the detected crosstalk event as an intrinsic event if the evoked response to the pacing pulse is not detected; and
adjusting the restarted pacing escape interval by the safety pace interval in response to reclassifying the detected crosstalk event as an intrinsic event.

15. The method of claim 14, further comprising adjusting a crosstalk detection criterion in response to reclassifying the detected crosstalk event.

16. The method of claim 10, further comprising:
increasing a count of detected crosstalk events in response to detecting the crosstalk event;
comparing the count to a crosstalk frequency threshold; and
adjusting a sensing control parameter in response to the count reaching the crosstalk frequency threshold.

17. The method of claim 10, further comprising:
determining an event interval from a preceding event to the detected crosstalk event;
comparing the determined event interval to a threshold interval; and
delivering a safety pacing pulse at a safety pace interval if the event interval is greater than the threshold interval.

18. The method of claim 10, further comprising automatically switching a pacing mode by the control module of the implantable pacemaker from an inhibiting mode to a non-inhibiting mode in response to detecting the crosstalk event.

* * * * *